United States Patent [19]

Carter

[11] 4,297,578
[45] Oct. 27, 1981

[54] AIRBORNE DUST MONITOR

[76] Inventor: William R. Carter, 5021 Wooddale La., Minneapolis, Minn. 55424

[21] Appl. No.: 110,601

[22] Filed: Jan. 9, 1980

[51] Int. Cl.$^3$ .......................... G01J 1/00; G01N 21/00
[52] U.S. Cl. ..................................... 250/343; 356/439
[58] Field of Search ............... 250/338, 343, 573, 574; 356/439

[56] References Cited

U.S. PATENT DOCUMENTS

| | | | |
|---|---|---|---|
| 2,406,409 | 8/1946 | Sheridan | 356/439 |
| 3,317,730 | 5/1967 | Hilsum | 250/343 |
| 3,809,913 | 5/1974 | Prellwitz | 356/439 |
| 3,854,045 | 12/1974 | Breuer et al. | 250/343 |

FOREIGN PATENT DOCUMENTS 55-1574  8/1980  Japan .................................. 356/439

*Primary Examiner*—Alfred E. Smith
*Assistant Examiner*—Janice A. Howell

*Attorney, Agent, or Firm*—Schroeder, Siegfried, Ryan, Vidas, Steffey & Arrett

[57] ABSTRACT

An airborne dust monitor. Photosensitive elements detect a predetermined airborne dust level at a test region adjacent the photosensitive elements. The photosensitive elements are housed within a flue which shields the test region from ambient light while it conducts ambient air through the test region. In a preferred embodiment, the flue is formed of generally vertical sidewall members which define an ambient air passage through the test region, air passage outlets positioned above the test region and a baffle generally at the inlet of the air passage for allowing the entry of ambient air to the passage while blocking light from the test region. A test system may be provided by which a member is selectively positionable within the test region. Preferably, the photosensitive detecting elements include a radiant energy source and an element responsive to that radiant energy, most preferably infrared energy, the photosensitive elements being positioned to minimize dust settlement on the acting portions thereof.

7 Claims, 1 Drawing Figure

AIRBORNE DUST MONITOR

DESCRIPTION

1. Background of Prior Art

Airborne dust is a problem in many environments. Such dust is created in the manufacturing and/or handling of many items. In some instances, it may be explosive, grain elevators being an example of long-standing concern from the standpoint of explosiveness of airborne dust. In other contexts, airborne dust may be injurious to the health of the workers either from the standpoint of excessive dust concentration or the nature of the dust itself, or both.

One prior art attempt to monitor dust known to the inventor is that disclosed in U.S. Pat. No. 2,406,409 issued Aug. 27, 1946, to H. W. Sheridan for DUST GAUGE. The Sheridan device employs a blower-induced air flow through a sinuous path one portion of which is probed by a beam of light. Light reflected from dust particles within the air flow is employed as a gauge of the amount of dust within the air sample.

The flow path of the Sheridan device employs many horizontal surfaces upon which dust may collect. Further, the optical elements within the flow path are positioned vertically and may, accordingly, themselves collect dust thereby affecting the sensitivity, and perhaps the operability, of the device. Finally, the use of a blower, and the attendant motor, introduces a potential source of electrical discharge into a potentially explosive atmosphere.

BRIEF SUMMARY OF THE INVENTION

The present invention provides a dust monitor for detecting predetermined levels of airborne dust at a test region. Photosensitive elements are positioned adjacent the test region and are housed within a flue which conducts ambient air through the test region. Additionally, the flue and cooperating structure shield the test region from ambient light. In a preferred embodiment, the flue is formed of generally vertical sidewalls which define on air passage through the test region, air passage outlets positioned above the test region and a baffle generally at the inlet of the air passage for allowing the entry of ambient air to the passage while blocking ambient light from the test region. Air flow through the test region is established without a blower or other driven member thereby eliminating the necessity for a potentially explosion-inducing motor. Provision is made to isolate the necessary electrical connections for the detecting components in a manner which minimizes their potential for explosion inducement. Also, the detecting elements are positioned so as to minimize the dust settlement on their active portions so as to enhance the reliability of the dust detection. In a preferred embodiment, the photosensitive detecting elements include a radiant energy source and a member responsive to that radiant energy, preferably infrared energy. A test member may be positioned selectively within the test region.

BRIEF DESCRIPTION OF THE DRAWINGS

The single FIGURE illustrates a side view, in partial cutaway, of a preferred embodiment of the present invention.

DETAILED DESCRIPTION OF THE DRAWINGS

Figure 1:
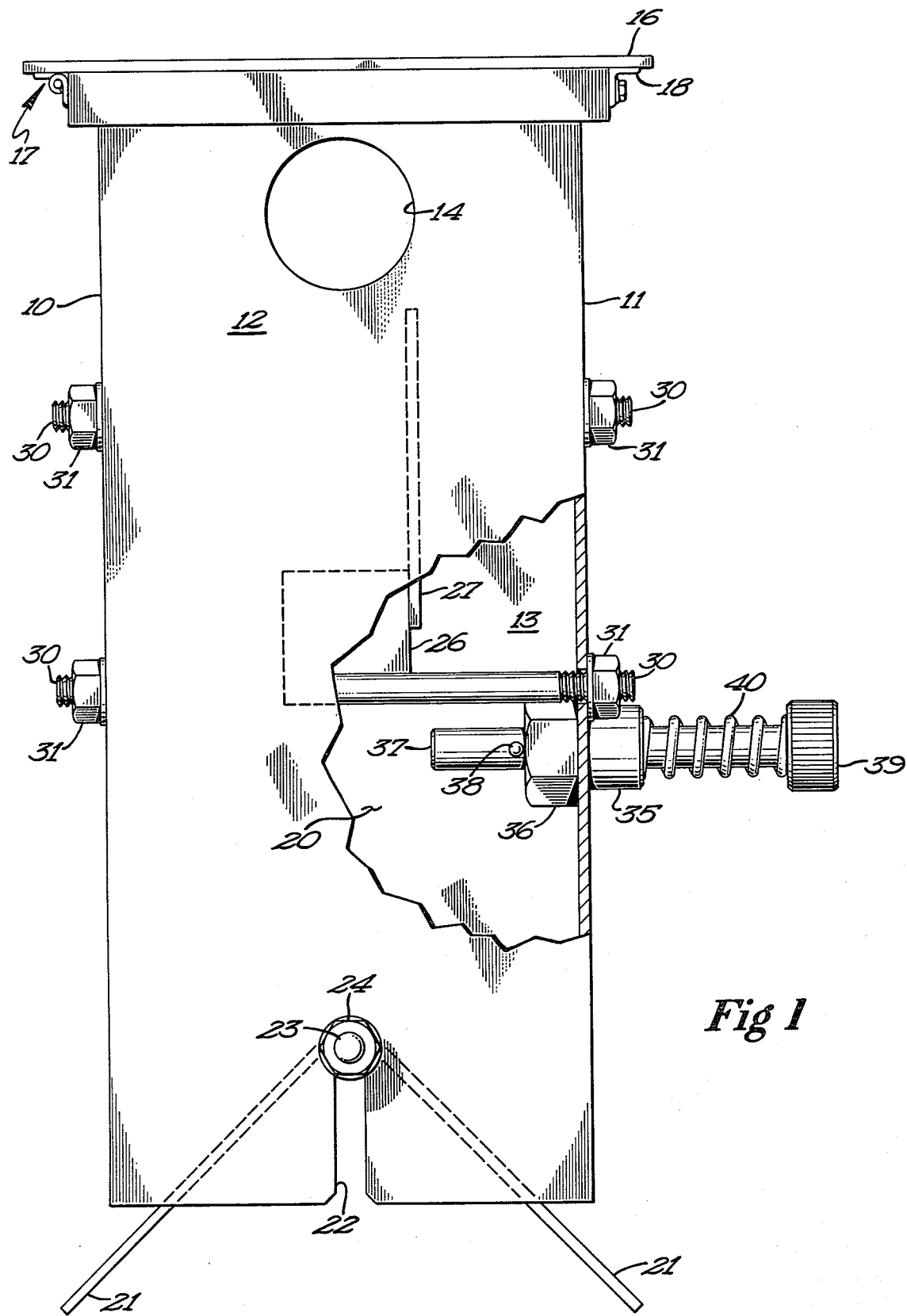

Referring now to the single FIGURE, there is illustrated a partial cutaway of a side view of a preferred embodiment of the present invention. A flue is formed of generally opposing sidewalls 10 and 11 and 12 and 13, respectively. Each of the sidewalls 10-13 may be provided with one or more outlet ports 14 (one illustrated) toward their upper end. The upper portion of the passageway defined by sidewalls 10-13 is blocked by a connection box 15 which may, itself, be explosion proof or which may house explosion-proof shields and in which electrical connections for the various electrical components employed within the present invention may be made, a wire or wires extending from the box 15 to the electrical components forming the detecting system being all that is exposed. For example, the box 15 may house an alarm, a power source or interconnections between a remote alarm and power source, in accordance with the desires of a particular application. A plate 16 is adapted to be secured to a ceiling or other supporting structure with the box 15 and plate 16 being hinged to each other as at 17. An angle 18 may be secured to the plate 16, as by welding one leg thereof to the plate 16, for example, with the other leg being secured to the box 15 in any desired manner, as through the use of threaded bolts, for example. With the box disengaged from its cooperating leg of angle 18, the box 15 and flue formed of sidewalls 10-13 may be pivoted around the hinge 17 to expose the inner portions of the box 15.

A test region at which the level of airborne dust is to be monitored is indicated generally at 20. The flue formed by the sidewalls 10-13 conducts ambient air through the test region 20 while shielding the test region 20 from ambient light. The ports 14 are positioned above the test region 20 to provide an outlet for the ambient air. A baffle 21 is provided at the inlet of the air passage defined by sidewalls 10-13 to allow entry of ambient air into the air passage, to flow through the test region 20, while shielding the test region 20 from ambient light.

The baffle 21 may be held in position in any desired manner. In the illustrated embodiment, sidewalls 12 and 13 are each provided with a slot 22 with a rod 23 being positioned within the slots 22 to extend past the outer surfaces of the sidewalls 12 and 13. Nuts 24, or any other desired fastener, engage the rod 23 and bear against the cooperating one of sidewalls 12 and 13 to maintain the rod 23 in position. Baffle 21 may be a unitary structure suspended over the rod 23.

Positioned adjacent to and above the test region 20 are the dust detecting elements illustrated diagrammatically as a detecting unit 26 and associated circuit board 27 which contains the electronic control elements for the unit 26. The detecting elements may be any suitable elements known to the prior art. It has been found that a smoke detector available from Radio Shack and identified as Stock No. 275-453, which is an infrared smoke detector, is acceptable for the present application with the housing removed, the detecting unit 26 and circuit board 27 being all that is employed. The unit 26 provides infrared energy at the test region 20 and contains a detector which is responsive to infrared energy which is reflected by dust in the test region. A predetermined dust level will result in an indication of any desired nature. The acting portions of detecting unit 26 (lenses, light transmission ports, etc.) are preferably positioned facing downward to minimize the amount of dust that settles thereon and, therefore, to reduce the effects of such dust settlement over time. A plurality of rods 30 and cooperating fasteners 31 may extend between sidewalls 10 and 11 to engage the detecting elements and support them within the passageway formed by the sidewalls 10-13. Alternatively, any other type of support may be employed.

At this point, there has been described a housing which supports a detecting assembly adjacent a test region while shielding the test region from ambient light and conducting ambient air through the test region. In many contexts, it may be desirable to provide a means by which the operation of the airborne dust monitor may be tested. A system for such a test is also illustrated in the single figure. A bearing 35 extends through a bore in sidewall 11 to present a threaded member within the passage formed by the sidewalls 10-13. A nut 36 engages the threaded portion of bearing 35 and, when tightened, secures the bearing to the sidewall 11. The bearing 35 is provided with a bore therethrough which accepts a rod 37. The rod 37 extends into the passageway formed by the sidewalls 10-13 and, within that passageway, carries a pin 38. The pin 38 will bear against the surface of the nut 36 to prevent a withdrawal of the rod 37 from the passageway. The end of the rod 37 outside of the passageway may be provided with a knob 39 with a compression spring 40 engaging the knob and bearing 35 to maintain the pin 38 normally in abutment with the nut 36. In this configuration, that portion of the rod within the passageway is normally outside of the test area 20. However, a force applied to the knob 39 may drive that portion of the rod 37 within the passageway into the test region 20 causing the detecting elements to sense its presence and give an indication. In this manner, the operation of the unit may be tested.

Obviously, many modifications and variations of the present invention are possible in light of the above teachings. For example, the monitor may give an onsight indication of the detection of a predetermined dust level within the test area 20 or may result in a remote indication. The indication may take the form of an alarm or a visual indication, or both. The detecting unit may be of any known photosensitive type with infrared having proven to be sufficiently sensitive and reliable. Of course, to enhance the reliability of the operation of the system, at least the inner surfaces of the unit should be non-reflective. It has been found that a dull black paint finish is sufficient. It is therefore to be understood that, within the scope of the appended claims, the invention may be practiced otherwise than as specifically described.

I claim:

1. In an airborne dust monitor of the type having photosensitive means for detecting a predetermined airborne dust level at a test region, the improvement which comprises generally vertical flue means for establishing a flow of ambient air through said test region, said detecting means being housed within said flue means adjacent said test region, and test means, including test element means, operable from the outside of said flue means for selectively positioning said test element means within said test region.

2. The airborne dust monitor of claim 1 wherein said flue means comprises generally vertical sidewall means defining an ambient air passage through said test region, air passage outlet means positioned above said test region and baffle means generally at the inlet of said air passage for allowing the entry of ambient air to said passage while blocking ambient light from said test region.

3. The airborne dust monitor of claim 2 wherein said photosensitive detecting means comprises radiant energy source means and means responsive to said radiant energy.

4. The airborne dust monitor of claim 3 wherein said radiant energy source and responsive means are positioned to minimize dust settlement on the acting portions thereof.

5. The airborne dust monitor of claim 4 wherein said radiant energy source and responsive means comprise infrared means.

6. The airborne dust monitor of claim 1 wherein said photosensitive detecting means is positioned to minimize dust settlement on the acting portions thereof.

7. The airborne dust monitor of claim 6 wherein said flue means comprises generally vertical sidewall means defining an ambient air passage through said test region, air passage outlet means positioned above said test region and baffle means generally at the inlet of said air passage for allowing the entry of ambient air to said passage while blocking ambient light from said test region.

* * * * *